United States Patent
Boyes et al.

(10) Patent No.: US 11,207,487 B2
(45) Date of Patent: Dec. 28, 2021

(54) SYSTEM FOR HUMIDIFICATION OF MEDICAL GASES

(71) Applicant: Fisher & Paykel Healthcare Limited, Auckland (NZ)

(72) Inventors: Richard John Boyes, Auckland (NZ); Christian Francis Fischer, Auckland (NZ); Charlotte Grace Laus, Auckland (NZ); Elmo Benson Stoks, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 483 days.

(21) Appl. No.: 16/071,186

(22) PCT Filed: Jan. 20, 2017

(86) PCT No.: PCT/NZ2017/050005
§ 371 (c)(1),
(2) Date: Jul. 19, 2018

(87) PCT Pub. No.: WO2017/126982
PCT Pub. Date: Jul. 27, 2017

(65) Prior Publication Data
US 2021/0077768 A1  Mar. 18, 2021
US 2021/0370012 A9  Dec. 2, 2021

Related U.S. Application Data

(60) Provisional application No. 62/281,632, filed on Jan. 21, 2016, provisional application No. 62/281,612, filed on Jan. 21, 2016.

(51) Int. Cl.
*A61M 16/16* (2006.01)
*A61M 16/10* (2006.01)
(Continued)

(52) U.S. Cl.
CPC ........ *A61M 16/16* (2013.01); *A61M 16/1095* (2014.02); *A61M 16/142* (2014.02);
(Continued)

(58) Field of Classification Search
CPC .............. A61M 16/00; A61M 16/1045; A61M 16/1075; A61M 16/1085; A61M 16/109;
(Continued)

(56) References Cited

U.S. PATENT DOCUMENTS 3,638,926 A * 2/1972 Melville ............... A61M 16/16
261/130
3,695,267 A * 10/1972 Hirtz ................... A61M 16/142
128/203.17
(Continued)

FOREIGN PATENT DOCUMENTS

GB          1485458      9/1977
WO    WO 2015/136489    9/2015
WO    WO 2016/125122    8/2016

*Primary Examiner* — Joseph D. Boecker
(74) *Attorney, Agent, or Firm* — Knobbe Martens Olson & Bear, LLP (57) ABSTRACT

A humidifier for delivering humidified gases to a patient includes an inlet, an outlet, a gases flow path extending from the inlet to the outlet, a permeable wall, a liquid reservoir, and a heater. The permeable wall separates the gases flow path from the liquid reservoir. The heater heats liquid stored in the liquid reservoir to form vapour, and the vapour passes through the permeable wall to the gases flow path to humidify gases in the gases flow path. Another inline humidifier for delivering humidified gases to a patient includes an inlet and an outlet and holds a tape made of hydrophilic or hygroscopic material. The tape is pre-soaked with water and can include a heating element. The heating element heats the tape and the stored water to release the stored water as vapour and thereby humidify gases passing through the inline humidifier.

22 Claims, 8 Drawing Sheets

(51) Int. Cl.
*A61M 16/14* (2006.01)
*A61M 13/00* (2006.01)

(52) U.S. Cl.
CPC ... *A61M 13/003* (2013.01); *A61M 2205/7536* (2013.01); *A61M 2206/12* (2013.01)

(58) Field of Classification Search
CPC .............. A61M 16/1095; A61M 16/14; A61M 16/142; A61M 16/16; A61M 13/003; A61M 2205/7536; A61M 2206/12; F24F 6/04; F24F 6/10
See application file for complete search history.

(56) References Cited

U.S. PATENT DOCUMENTS

| | | | | |
|---|---|---|---|---|
| 2006/0012057 | A1* | 1/2006 | Anthony | A61M 16/16 261/154 |
| 2008/0262377 | A1* | 10/2008 | Belson | A61M 16/1075 600/549 |
| 2009/0038614 | A1* | 2/2009 | Kuo | A61M 16/16 128/203.26 |
| 2011/0106001 | A1* | 5/2011 | Ott | A63B 51/10 604/24 |
| 2014/0232024 | A1* | 8/2014 | Church | A61M 16/0875 261/141 |
| 2015/0196323 | A1 | 7/2015 | Koeth | |
| 2017/0007798 | A1* | 1/2017 | Salmon | A61M 16/04 |

* cited by examiner

SYSTEM FOR HUMIDIFICATION OF MEDICAL GASES

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application claims priority to U.S. Provisional Application No. 62/281,632, filed Jan. 21, 2016, and U.S. Provisional Application No. 62/281,612, filed Jan. 21, 2016, each of which is hereby incorporated by reference in its entirety.

BACKGROUND

Field

The present disclosure generally relates to a system for the humidification of medical gases. More particularly, the present disclosure relates to a system for the humidification of medical gases using an inline humidifier.

Description of the Related Art

A humidification apparatus can be used to provide heated and humidified gases to a patient via a patient interface for various purposes, including respiratory therapy and laparoscopic procedures. In laparoscopic procedures, humidified medical gases help protect the peritoneum from desiccation and inflammation that can be caused by cold dry gases used during surgical procedures.

Pass-over humidification devices supply heated, humidified gases to a patient. Such humidification systems typically comprise a humidification apparatus, a humidification chamber, a tube system, and a patient interface. The humidification apparatus comprises a heater plate that is configured to heat the humidification chamber. This causes vapour to form, which enters a flow of gases flowing through the humidification chamber, humidifying the medical gases. Such humidification systems can have a large footprint and require large volumes of liquid for humidification to take place. Heat is applied to the heater plate of the humidification chamber to form vapour, meaning the heater plate is hot to touch.

Humidification systems for surgical applications may comprise a tube with a wicking or absorptive material positioned within the gases flow path. The wicking or absorptive material connects with an external liquid supply or reservoir, and liquid travels along the wick to the gases flow path, for example, via capillary action. Heat is applied to the wicking material, releasing vapour into the gases flow path in the tube. Some humidification systems hold liquid within compartments or reservoirs within the tube. Heat is applied to the liquid to form vapour, and the vapour moves through a permeable membrane into the lumen of the tube.

An external liquid supply reduces the portability of the humidification system, increases the number of set-up steps, and thus increases the overall complexity of the system. A system with an external liquid supply also typically requires a large portion of the limited space within a surgical theatre.

Liquid held in reservoirs within the tube increases the weight and reduces the flexibility of the tube, thereby making the tube difficult to manipulate within the surgical space.

SUMMARY

According to a first aspect, a humidifier is provided comprising an inlet and an outlet and a gases flow path extending from the inlet to the outlet; a liquid reservoir; in thermal communication with; or configured to be in thermal communication with in use, a heater; and a permeable wall separating the liquid reservoir from the gases flow path; wherein, in use, the heater heats liquid stored in the liquid reservoir to form vapour, and the vapour passes through the permeable wall to humidify gases in the gases flow path.

The reservoir is preferably configured to hold sufficient liquid to produce vapour for an intended volume of gases passing through the humidifier.

The gases flow path is preferably defined, at least in part, by a spirally wound wall within the housing.

The humidifier may comprise a hydrophobic housing.

The humidifier preferably comprises a tape. More preferably, the permeable wall comprises a tape. The tape preferably comprises a hydrophilic material.

The heater may include one or more heater wires or elements and may be provided inside the humidifier (i.e. in close proximity to the reservoir) or adjacent a surface thereof, such as the base. Alternatively, the humidifier may be configured to thermally couple with a heater so as to receive heat from another source. For example, a more conventional humidifier heater arrangement could be used where the humidifier is adapted to sit on and/or abut a heater plate. Preferably, where heater elements are positioned outside of the humidifier, walls of high thermal conductivity are provided to facilitate heat transfer to the reservoir. Such walls or parts thereof may, for example, be formed from a metal such as aluminium.

According to a second aspect, there is provided a humidifier comprising a housing having an inlet and an outlet; and a tape disposed within the housing and at least partially defining a gases flow path through the housing between the inlet and the outlet, wherein the tape comprises a hydrophilic material configured to hold a volume of liquid and a heating mechanism configured to heat liquid held within the hydrophilic material to produce vapour.

The hydrophilic material is preferably configured to hold sufficient liquid to produce vapour for an intended volume of gases passing through the humidifier. The hydrophilic material may be configured to be pre-loaded prior to use to cause liquid to be held within the hydrophilic material.

The tape may be spirally wound within the housing.

The housing may comprise a hydrophobic material.

The heating mechanism preferably comprises at least one heater wire disposed within and surrounded by the hydrophilic material. However, other heating arrangements are possible in the same manner as stated in respect of the first aspect.

The invention also provides a humidification system comprising the humidifier of the first aspect and/or the second aspect. For humidification systems comprising both the first and second aspects, preferably, the wall comprises a tape and/or a tape is positioned adjacent or affixed to the wall.

The humidification system preferably comprises a delivery tube coupled to the outlet and configured to, at least in part, transport gases from the housing to a patient in use.

There is also provided a humidification system comprising a humidifier comprising an inlet and an outlet and a gases flow path extending from the inlet to the outlet; a liquid reservoir; a heater in thermal communication with the liquid reservoir; and a permeable wall separating the liquid reservoir from the gases flow path; wherein in use, the heater heats liquid stored in the liquid reservoir to form vapor, and the vapor passes through the permeable wall to humidify gases in the gases flow path; and a delivery tube coupled to the outlet and configured to transport gases from the housing to a patient in use.

The liquid reservoir may be configured to hold sufficient liquid to produce vapour for an intended volume of gases passing through the humidification system.

The gases flow path may be defined by a spirally wound wall within the housing.

The humidifier may comprise a hydrophobic housing.

The delivery tube may comprises a second heating mechanism. The second heating mechanism may comprise at least one heater wire disposed within the delivery tube.

There is also provided a humidification system comprising a humidifier comprising a housing having an inlet and an outlet; and a tape disposed within the housing and at least partially defining a gases flow path through the housing between the inlet and the outlet, wherein the tape comprises a hydrophilic material configured to hold a volume of liquid and a heating mechanism configured to heat liquid held within the hydrophilic material to produce vapour; and a delivery tube coupled to the outlet and configured to transport gases from the housing to a patient in use.

The hydrophilic material may be configured to hold sufficient liquid to produce vapour for an intended volume of gases passing through the humidification system.

The hydrophilic material may be configured to be pre-loaded prior to use to cause liquid to be held within the hydrophilic material.

The tape may be spirally wound within the housing.

The housing may comprise a hydrophobic material.

The heating mechanism may comprise at least one heater wire disposed within and surrounded by the hydrophilic material.

The delivery tube may comprise a second heating mechanism. The second heating mechanism may comprise at least one heater wire disposed within the delivery tube.

A humidification system is disclosed that comprises an inline (i.e., in line with a delivery tube or conduit) humidifier to provide heated and humidified gases to a patient. The humidification system advantageously requires reduced or minimal set-up steps due to the inline humidifier design. For example, there is no need for an external liquid reservoir to supply the system with sufficient liquid for the surgical procedure. Similarly, there is no need for a wick to convey liquid into the tube so that humidification can take place. The inline humidifier and tube are not dependent on a specific orientation for functionality, which gives the medical practitioner more freedom to manipulate the system.

In some embodiments, a humidification system includes a humidifier and a delivery tube. The humidifier includes a housing having an inlet and an outlet and a tape disposed within the housing. The tape at least partially defines a gases flow path through the housing between the inlet and the outlet. The tape can include a hydrophilic or hygroscopic material configured to hold a volume of liquid and a heating mechanism to heat liquid held within the hydrophilic or hygroscopic material to produce vapour. The delivery tube is coupled to the outlet and is configured to transport gases from the housing to a patient in use.

In some embodiments, the hydrophilic or hygroscopic material is configured to hold sufficient liquid to produce vapour for an intended volume of gases passing through the humidification system. In some embodiments, the hydrophilic or hygroscopic material is configured to be pre-loaded prior to use to cause liquid to be held within the material. In some embodiments, the tape is spirally wound within the housing. In some embodiments, the housing comprises a hydrophobic material. In some embodiments, the heating mechanism comprises at least one heater wire disposed within and surrounded by the hydrophilic or hygroscopic material. The delivery tube can include a second heating mechanism. In some embodiments, the second heating mechanism comprises at least one heater wire disposed within the delivery tube.

In some embodiments, a humidifier includes a housing having an inlet and an outlet and a tape disposed within the housing. The tape at least partially defines a gases flow path through the housing between the inlet and the outlet. The tape includes a hydrophilic or hygroscopic material configured to hold a volume of liquid and a heating mechanism configured to heat liquid held within the hydrophilic material to produce vapour. In some embodiments, the hydrophilic or hygroscopic material is configured to hold sufficient liquid to produce vapour for an intended volume of gases passing through the humidification system. In some embodiments, the hydrophilic or hygroscopic material is configured to be pre-loaded prior to use to cause liquid to be held within the material. In some embodiments, the tape is spirally wound within the housing. In some embodiments, the housing comprises a hydrophobic material. In some embodiments, the heating mechanism comprises at least one heater wire disposed within and surrounded by the hydrophilic or hygroscopic material.

In some embodiments, a humidification system includes a humidifier and a delivery tube. The humidifier includes an inlet, an outlet, a gases flow path extending from the inlet to the outlet, a liquid reservoir, a heater in thermal communication with the liquid reservoir, and a permeable wall separating the liquid reservoir from the gases flow path. In use, the heater heats liquid stored in the liquid reservoir to form vapor, and the vapor passes through the permeable wall to humidify gases in the gases flow path. The delivery tube is coupled to the outlet and configured to transport gases from the housing to a patient in use.

In some embodiments, the liquid reservoir is configured to hold sufficient liquid to produce vapour for an intended volume of gases passing through the humidification system. In some embodiments, the gases flow path is defined by a spirally wound wall within the housing. In some embodiments, the humidifier comprises a hydrophobic housing. The delivery tube can include a second heating mechanism. In some embodiments, the second heating mechanism comprises at least one heater wire disposed within the delivery tube.

In some embodiments, an inline humidifier includes an inlet, an outlet, a gases flow path extending from the inlet to the outlet, a liquid reservoir, a heater in thermal communication with the liquid reservoir, and a permeable wall separating the liquid reservoir from the gases flow path. In use, the heater heats liquid stored in the liquid reservoir to form vapor, and the vapor passes through the permeable wall to humidify gases in the gases flow path.

In some embodiments, the liquid reservoir is configured to hold sufficient liquid to produce vapour for an intended volume of gases passing through the humidification system. In some embodiments, the gases flow path is defined by a spirally wound wall within the housing. In some embodiments, the humidifier comprises a hydrophobic housing.

DETAILED DESCRIPTION

Figure 1:
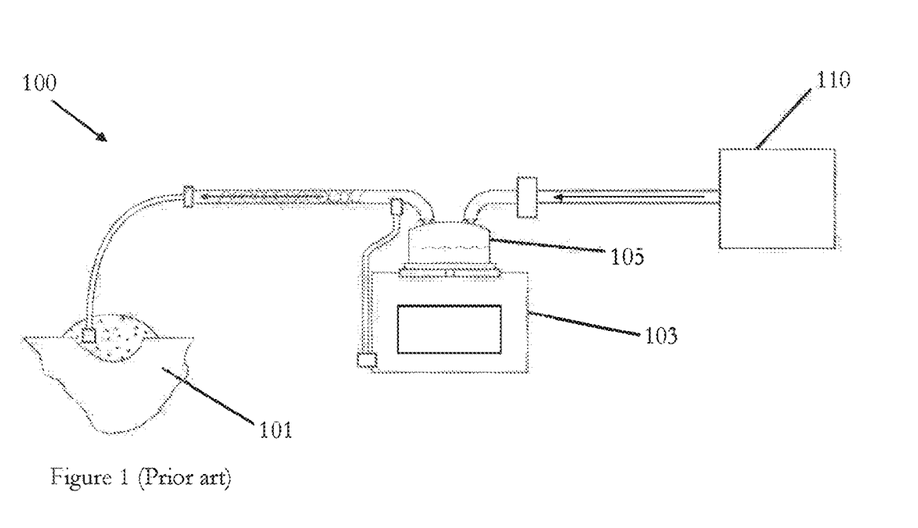
FIG. 1 illustrates a schematic of a prior art humidification system.

FIG. 1 illustrates a prior art humidification system 100 that is configured to deliver heated and humidified gases to a patient 101. The humidification system 100 comprises a humidification apparatus 103, a humidification chamber 105, and a gases source 110. In an embodiment, the gases source 110 is an insufflator. The humidification chamber 105 is configured to hold a volume of liquid, such as water. The humidification apparatus 103 comprises a heating mechanism configured to heat the water within the humidification chamber 105 to form water vapour. Gases from the gases source 110 are heated and humidified as they pass through the humidification chamber 105, and the conditioned gases are delivered to the patient 101.

Gases as herein described refers to respiratory gases (for example, oxygen, air, nitrogen, carbon dioxide, or a combination of any of these), or surgical gases, (for example, carbon dioxide, nitrous, oxygen, air, helium, or a mixture of carbon dioxide with nitrous or oxygen). Other gases or combinations of gases also fall within the scope of the disclosed apparatus and systems.

Figure 2:
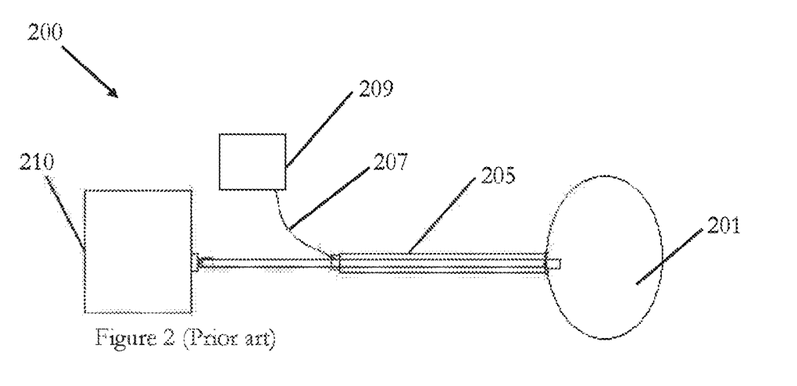
FIG. 2 illustrates a schematic of a prior art tube humidification system.

FIG. 2 illustrates a prior art humidification system 200 that is configured to deliver heated and humidified gases to a patient 201. The humidification system 200 comprises a tube humidifier 205, a water channel 207, a water supply 209, and a gases source 210. In an embodiment, the gases source 210 is an insufflator. Gases from the gases source 210 are delivered to the patient 201 via the tube humidifier 205. The tube humidifier 205 comprises a wicking membrane that wicks water via the water channel 207 from the water supply 209. The wicked water is heated using a heating mechanism, thereby causing evaporation of the water. The water vapour generated enters the lumen of the tube humidifier 205, thereby causing the gases flowing therein to become humidified. The humidified gases are delivered to the patient 201.

As explained herein, humidification systems such as the system 100 and the system 200 require external liquid supplies (such as liquid supplies in the humidification chamber 105 or the water supply 209), which can decrease the portability and maneuverability of the system, increase the number of set-up steps, and increase the footprint of the system.

Figure 3:
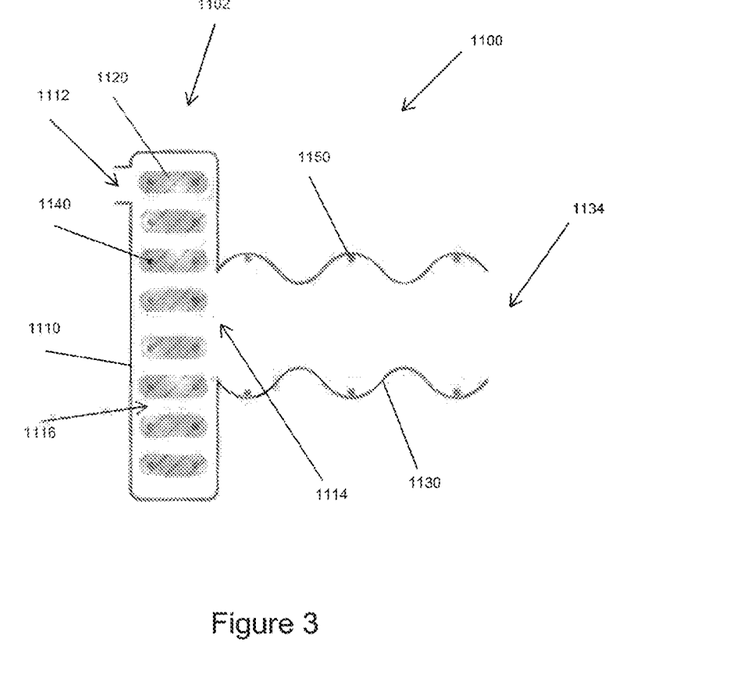
FIG. 3 illustrates a longitudinal cross-sectional view of a schematic of an example embodiment of a humidification system including an inline humidifier.

FIG. 3 illustrates a side or longitudinal cross-sectional view of an example embodiment of a humidification system 1100 including an inline humidifier 1102 according to the present disclosure. As shown, the humidification system 1100 includes the inline humidifier 1102 and a delivery tube or conduit 1130. The inline humidifier 1102 includes a housing 1110, a tape 1120, and one or more heating elements 1140. The housing 1110 has a gases inlet 1112 and a gases outlet 1114. The gases outlet 1114 is coupled to a first end of the delivery tube 1130 in use. In some embodiments, the delivery tube 1130 is permanently coupled to the gases outlet 1114. In some embodiments, the delivery tube 1130 can be removably coupled to the gases outlet 1114. The delivery tube 1130 can be provided preassembled to the gases outlet 1114. An opposite, second end 1134 of the delivery tube 1130 can be coupled to a patient interface, for example, a laparoscopic cannula, or another humidification system component in use. In some embodiments, the humidification system 1100 is disposable. In other embodiments, the humidification system 1100 can be refillable and/or sterilisable for reuse.

The housing 1110 can be made of a hydrophobic or any other gases and/or water impermeable or low permeability material. In some embodiments, the housing 1110 includes insulation to reduce or minimize heat transfer with the external environment or atmosphere. In the illustrated embodiment, the housing 1110 is generally disc-shaped or circular. However, other shapes are also possible, for example, quadrilateral, square, trapezoidal, parallelogram, or other shapes. The gases inlet 1112 is disposed on a front side or face of the housing 1110, and the gases outlet 1114 is disposed on an opposite rear side or face of the housing 1110. In other embodiments, the gases inlet 1112 can be disposed on a rear side of the housing 1110 or on a side or edge of the housing 1110 and/or the gases outlet 1114 can be disposed on a front side of the housing 1110 or on a side or edge of the housing 1110. As shown in FIG. 3 and the front (viewed from the left of FIG. 3) view of the humidifier 1102 shown in FIG. 4, the gases inlet 1112 can be positioned proximate an outer perimeter of the front side of the housing 1110 or closer to the outer perimeter than a center of the front side of the housing 1110. As shown in FIG. 3 and the rear (viewed from the right of FIG. 3) cross-sectional view of the humidification system 1100 shown in FIG. 5, the gases outlet 1114 can be positioned at or proximate a center of the rear side of the housing 1110. In other embodiments, the gases inlet 1112 can be positioned proximate the center of the housing 1110 and the gases outlet 1114 can be positioned proximate the outer perimeter of the housing 1110, both the gases inlet 1112 and the gases outlet 1114 can be positioned proximate the center of the housing 1110, both the gases inlet 1112 and the gases outlet 1114 can be positioned proximate the outer perimeter of the housing 1110, or the gases inlet 1112 and the gases outlet 1114 can be positioned at any position between the center and outer perimeter on either side of the housing 1110.

The tape 1120 can include or be made of a hydrophilic or hygroscopic material that can absorb and/or retain a volume of liquid, such as water. A hygroscopic material attracts and holds water molecules via adsorption. A hygroscopic material can be porous, for example, like silica gel or zeolite, and/or can have surface features to increase the effective area of the material. A hydrophilic material absorbs water in a vapor and/or liquid state. A hydrophilic material can be foamed and/or can include surface features to increase the effective area of the material. For example, in some embodiments, the tape 1120 can be made of Arnitel or another hydrophilic material.

The tape 1120 can include the heating elements 1140. The heating elements 1140 can be placed within, on, or surrounding the tape 1120. In the illustrated embodiment, the heating elements 1140 of the tape 1120 include two heater wires disposed within and surrounded by the hydrophilic or hygroscopic material. In use, heat from the heating elements 1140 causes vapor to be released from the hydrophilic or hygroscopic material of the tape 1120.

The tape 1120 is disposed within the housing 1110 and arranged to define a gases flow path 1116 within the housing 1110 between the gases inlet 1112 and the gases outlet 1114. The tape 1120 can be spirally wound within the housing 1110 as shown. Other arrangements for the tape 1120 within the housing 1110 are also possible. A configuration or arrangement of the tape 1120 that creates a convoluted embodiment of the gases flow path 1116 can increase the degree or level of water vapor exchange as described in greater detail herein. In some embodiments, extrusions of a hydrophilic or hygroscopic material are arranged in a random, tangled manner in the housing 1110, similar to a bird nest. Gases can flow freely through spaces between the extrusions of hydrophilic or hygroscopic material from the gases inlet 1112 to the gases outlet 1114. The hydrophilic or hygroscopic material can be heated by a heater plate or one or more heater wires disposed within the housing 1110. In some embodiments, the tape 1120 can be arranged to form a 3D spiral arrangement of the gases flow path 1116, similar to a corkscrew. In some such embodiments, the housing 1110 can include an internal liquid reservoir within the internal volume of the corkscrew.

Figure 4:
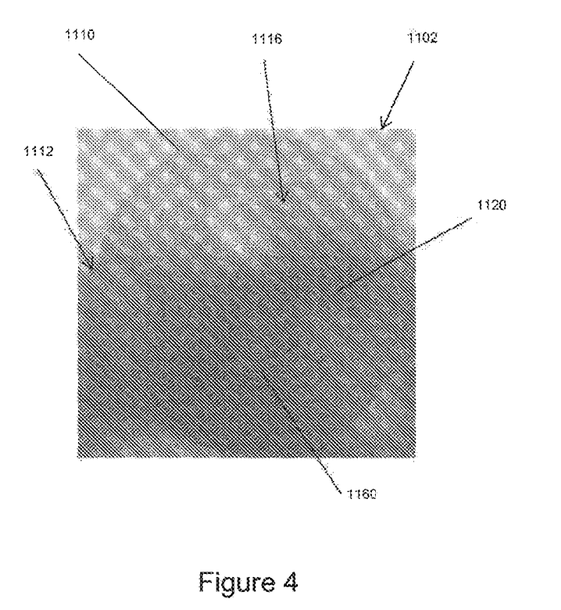
FIG. 4 illustrates a front view of the humidifier of FIG. 3.
Figure 5:
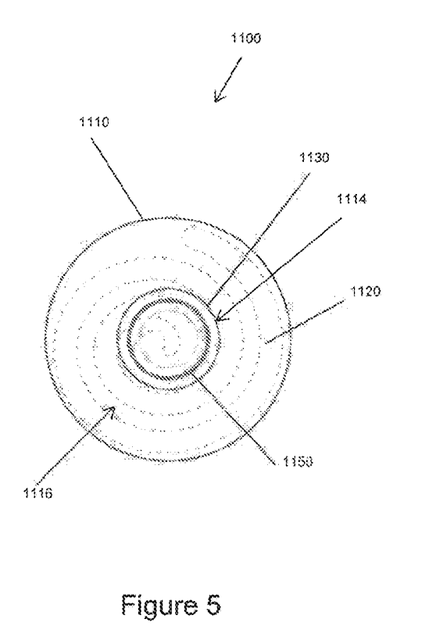
FIG. 5 illustrates a rear cross sectional view of the humidification system of FIG. 3.

In some embodiments—for example, in the illustrated embodiment in which the tape 1120 is arranged in a spiral, the gases inlet 1112 is positioned proximate the outer perimeter of the housing 1110, and the gases outlet 1114 is positioned proximate the center of the housing 1110—the gases flow path 1116 follows a spiral path from an outer perimeter of the housing 1110 to a center of the housing 1110. In such an arrangement, gases in the gases flow path 1116 warm as the gases travel inward toward the center of the housing 1110 and to the gases outlet 1114, and the gases are insulated by gases in portions of the gases flow path 1116 disposed concentrically outward. If the gases flow path 1116 instead followed a path from the center of the housing 1110 to the perimeter of the housing 1110, the warmest gases at the end of the gases flow path 1116 and at the gases outlet 1114 would be at the outer perimeter of the housing 1110 and therefore less insulated, which could reduce the efficiency of the system. A spiral arrangement of the gases flow path 1116 can advantageously reduce or minimize flow dead spots in which the flow of gases recirculates or slows. The tape 1120 can be retained within the housing 1110 and/or retained in the spiral or other arrangement by clips or other retainers 1160, as shown in FIG. 4.

The humidification system 1100 or the humidifier 1102 can be supplied sterilized and ready for use. The humidification system 1100, specifically the tape 1120, can be preloaded (e.g., during manufacturing and assembly or setup) with a volume of liquid, such as water (e.g., in liquid form in a hygroscopic material or in liquid and/or vapor form in a hydrophilic material) prior to a surgical procedure or other use. In some embodiments, the tape 1120 can hold approximately 30% weight in water after a soak time of one hour. The tape 1120 can be pre-soaked with a known and desired quantity of liquid, which can be calculated based on the average duration of a typical procedure for which the humidification system 1100 is intended to be used. The humidification system 1100 therefore does not require a separate liquid reservoir or delivery system, and medical personnel need not input liquid into the system prior to use during set-up. In some embodiments, the humidifier 1102 can be refilled after use for re-use or during use if needed.

In use, gases enter the housing 1110 through the gases inlet 1112, flow through the gases flow path 1116, exit the housing 1110 through the gases outlet 1114, flow through the delivery tube 1130, and are delivered to a patient, patient interface connector, or other humidification system component at the second end 1134. Power is supplied to the heating elements 1140 such that the heating elements 1140 heat the liquid or vapor stored within the tape 1120 to release vapor into the gases flow path 1116. Gases flowing through the gases flow path 1116 are therefore humidified by the vapor released from the tape 1120. The heated vapor can also heat the gases flowing through the gases flow path 1116. The heating elements 1140 can also directly heat the gases flowing through the gases flow path 1116. The configuration of the heating elements 1140 can affect the conditions of the gases exiting the gases flow path 1116. The size and type of the heating elements 1140 can be determined based on the geometry of the tape 1120 and how the geometry affects the humidification of heated gases. The hydrophobic, impermeable, or low permeability material of the housing 1110 can help hold the vapor within the housing 1110 to prevent or inhibit the vapor from being released through the housing 1110 to the atmosphere.

The tape 1120 can be an extruded polymer. A cross-sectional shape of the tape 1120 can be selected to optimize various factors, for example, to increase or maximize the surface area of the tape 1120 exposed to the gases flow path 1116 to increase the level of vapor exchange into gases in the gases flow path 1116. In the illustrated embodiment, the cross-sectional shape of the tape 1120 is rectangular or generally rectangular. In other embodiments, the tape 1120 has an elliptical or other cross-sectional shape.

Figures 6A, 6B:
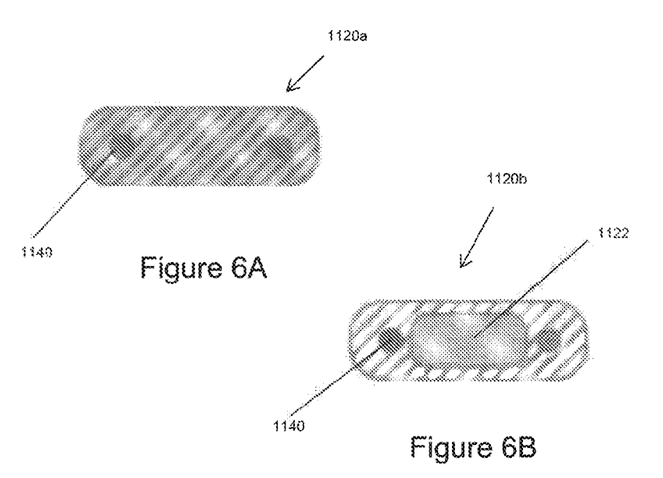
FIGS. 6A-6C illustrate cross-sectional views of schematics of various embodiments of tapes that can be included in the humidifier of FIGS. 3-5.
Figure 6C:
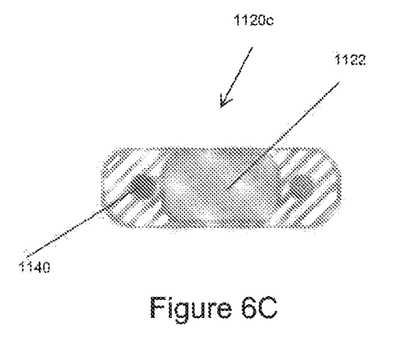

FIG. 6A illustrates a cross-sectional view of a tape 1120a, an embodiment of the tape 1120 as used in the embodiment of FIGS. 3-5. The hydrophilic or hygroscopic material of the tape 1120a has been pre-soaked with liquid such as water. FIGS. 6B-6C illustrate schematic cross-sectional views of a tape 1120b and a tape 1120c, which are alternative embodiments of the tape 1120.

The tape 1120b of FIG. 6B includes an internal liquid reservoir or cavity 1122 within the hydrophilic or hygroscopic material of the tape 1120b. In this embodiment, the hydrophilic or hygroscopic material might not be pre-soaked. Instead, in use, heat from the heating elements 1140 causes the liquid within the reservoir 1122 to vaporize, and the vapor permeates through the hydrophilic or hygroscopic material of the tape 1120b into the gases flow path 1116. The liquid reservoir 1122 may be able to be filled more quickly than the hydrophilic or hygroscopic material of the tape 1120b can absorb liquid via pre-soaking. The liquid reservoir 1122 may therefore reduce manufacturing or assembly time. In some embodiments, the tape 1120b can include the internal reservoir 1122 and the hydrophilic or hygroscopic material can be pre-soaked so that both the liquid absorbed by the hydrophilic or hygroscopic material and the liquid in the reservoir 1122 can contribute to the humidification of gases in the gases flow path 1116.

The tape 1120c of FIG. 6C also includes an embodiment of the internal liquid reservoir 1122. In this embodiment, the walls of hydrophilic or hygroscopic material of the tape 1120c surrounding the reservoir 1122 are thinner than those of the embodiment of FIG. 6B. Thinner walls of the tape 1120c can allow liquid from the reservoir 1122 to permeate the hydrophilic or hygroscopic material and vapor to transfer to the gases flow path 1116 more readily. Alternatively, thicker walls, as in the embodiment of FIG. 6B, can provide more structural strength to the tape 1120b.

The liquid reservoir 1122 can be filled and/or refilled in various ways, for example, by injecting, pumping, or pouring liquid into the reservoir 1122. In some embodiments, a vacuum can be generated within the reservoir 1122 by liquid in the reservoir 1122 becoming vapor and passing through the tape 1120 into the gases flow path 1116. The vacuum can provide a pressure differential to allow for refilling of the reservoir 1122. The reservoir 1122 can also or alternatively be refilled using a water or other liquid bag.

In use, the humidified and/or heated gases flowing through the gases flow path 1116 exit the housing 1110 through the gases outlet 1114 and flow into and through the delivery tube 1130. As shown in FIG. 3, the delivery tube 1130 can also include one or more heating elements 1150. The heating elements 1150 can heat and/or help maintain a temperature of the humidified gases flowing through the delivery tube 1130 to a patient. The humidification system 1100 therefore can employ a two-stage heating process. The humidifier 1102 can generate humidity at a reasonably or generally consistent absolute humidity level based on the amount of energy or power supplied to the heating elements 1140 of the humidifier 1102. Subsequently, the heating elements 1150 in the delivery tube 1130 can help maintain the temperature of the gases to deliver humidity to a patient at a reasonably or generally consistent relative humidity level.

In some embodiments, vapor can be released from a hydrophilic embodiment of the tape 1120 passively and/or without requiring heat. The heating elements 1140 therefore may not be required or included in the humidifier 1102. In some such embodiments, a concentration gradient drives movement of the water or vapor from the hydrophilic material of the tape 1120 to the gases flow path 1116.

The humidification system 1100 can include a control system. The humidification system 1100 can include a power source for supplying power to the heating elements 1140, 1150 and/or the control system. The control system can control the power supplied to the heating elements 1140 to control the amount of heat provided by the heating elements 1140, which in turn controls or affects the amount of vapor released from the tape 1120. The humidifier 1102 therefore provides for passive water vapor delivery and does not require active control of the vapor delivery.

The control system and/or power source can be external to the humidifier 1102 and/or the delivery tube 1130. The control system and/or power source can be housing within or integrated into a single housing or component. In some embodiments, the control system and/or power source can be mounted to a surgical tower or an insufflator. In some embodiments, the control system and/or power source can be connected to and receive power from a wall outlet.

Figure 7:
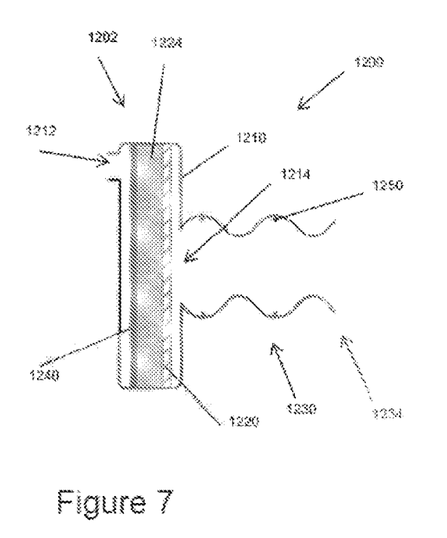
FIG. 7 illustrates a longitudinal cross-sectional view of a schematic of an example embodiment of a humidification system including an inline humidifier.
Figure 8:
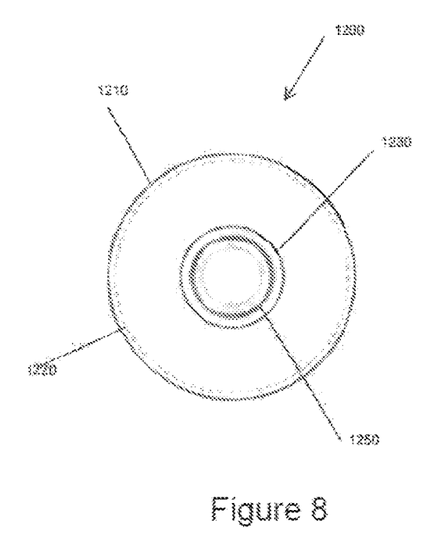
FIG. 8 illustrates a rear cross sectional view of the humidification system of FIG. 7.

FIGS. 7 and 8 illustrate an example embodiment of a humidification system 1200 including an inline humidifier 1202 according to the present disclosure. As shown, the humidification system 1200 includes the inline humidifier 1202 and a delivery tube or conduit 1230. In the illustrated embodiment, the inline humidifier 1202 is generally disc-shaped or circular. However, other shapes are also possible, for example, quadrilateral, square, trapezoidal, parallelogram, or other shapes. The inline humidifier 1202 advantageously allows the humidification system 1200 to have a smaller footprint than prior art humidification systems such as those shown in FIGS. 1 and 2.

Figure 10:
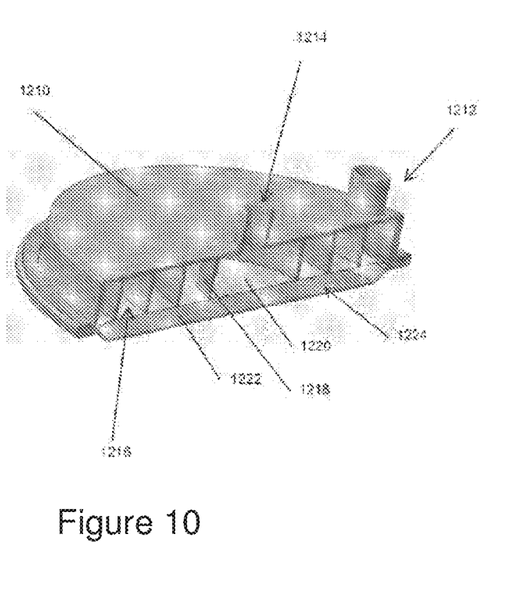
FIG. 10 illustrates a transverse or diametrical cross-sectional view of the humidifier of FIG. 9.

As shown in FIGS. 7 and 10, the inline humidifier 1202 includes a housing or cover 1210, a permeable wall or membrane 1220, a liquid reservoir 1224, a gases flow path 1216, and a heater. In some embodiments, as shown in FIG. 7, the inline humidifier 1202 includes a heater plate 1240, and the housing 1210 entirely surrounds other components of the inline humidifier 1202, including the heater plate 1240. In some embodiments, as shown in FIG. 10, the inline humidifier 1202 includes a base 1222 that is coupled to the housing 1210 and that acts as a heater. The permeable wall 1220 is positioned between the housing 1210 and the base 1222 as shown. In the illustrated embodiment, the gases flow path 1216 is bordered by the housing 1210 and the permeable wall 1220, and the liquid reservoir 1224 is bordered by the permeable wall 1220 and the base 1222. The base 1222 can be made from or include a material that is hydrophobic or liquid impermeable to contain the liquid within the reservoir 1224 and that is thermally conductive such that the base 1222 can act as the heater. For example, the base 1222 can be made of a metal such as aluminium. In some embodiments, the base 1222 is made of a combination of thermally conductive materials, such that the base 1222 can act as a heater, and thermally insulating materials, to help control or limit heat loss to the surrounding environment or atmosphere.

Outer edges or perimeters of the housing 1210 and the base 1222 can be coupled together to encase the permeable wall 1220, the liquid reservoir 1224, and the gases flow path 1216. The housing 1210 and the base 1222 can be coupled together via an adhesive, welding, crimping or bending the edges together, or any other suitable means. As shown in FIG. 10, the edges of the housing 1210, the base 1222, and the permeable wall 1220 can be folded or crimped together with the edges of the permeable wall 1220 sandwiched between the edges of the housing 1210 and the edges of the base 1222.

The inline humidifier 1202 has a gases inlet 1212 and a gases outlet 1214. The gases inlet 1212 can be coupled directly to an insufflator outlet port or can be coupled to the insufflator outlet port via a supply tube or conduit. The gases outlet 1214 is coupled to a first end of the delivery tube 1230 in use. In some embodiments, the delivery tube 1230 is permanently coupled to the gases outlet 1214. In some embodiments, the delivery tube 1230 can be removably coupled to the gases outlet 1214. The delivery tube 1230 can be provided preassembled to the gases outlet 1214. An opposite, second end 1234 of the delivery tube 1230 is coupled to a patient interface, for example, a laparoscopic cannula, or another humidification system component in use. In some embodiments, the humidification system 1200 is disposable. In other embodiments, the humidification system 1200 can be refillable and/or sterilisable for reuse.

Figure 9:
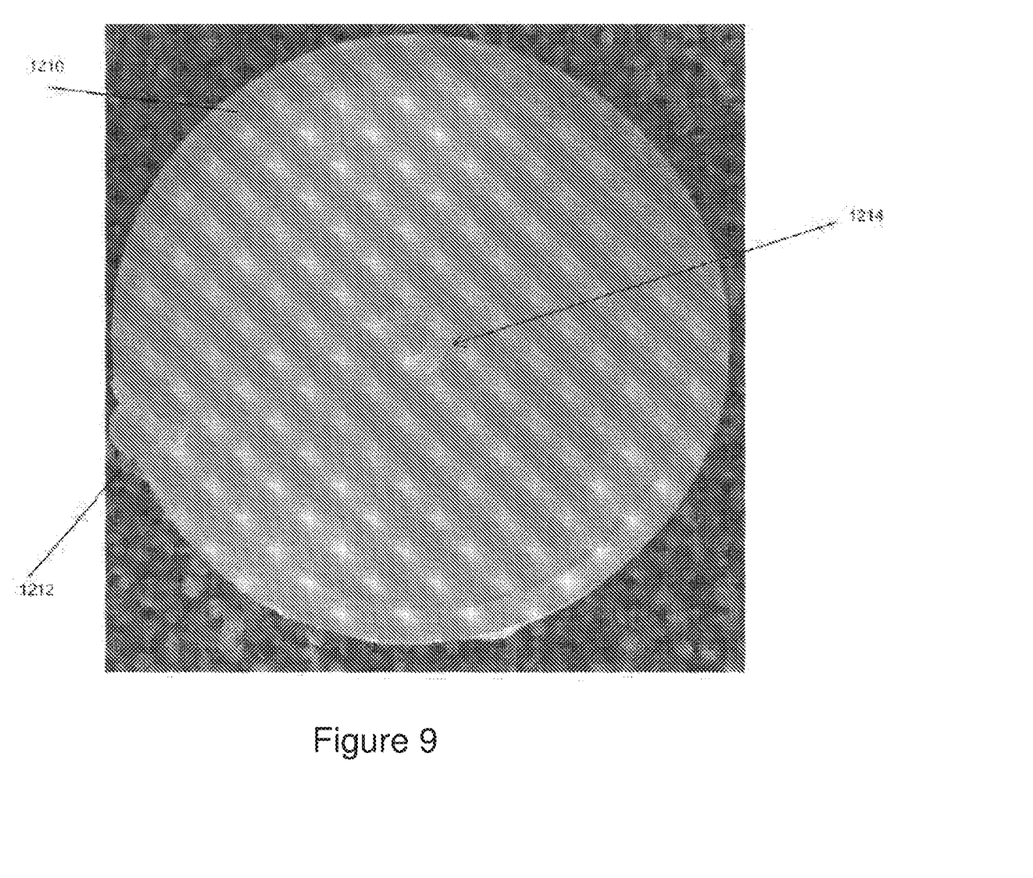
FIG. 9 illustrates a rear view of an example embodiment of a humidifier for use with the humidification system of FIG. 7.

The housing 1210 can be made of a hydrophobic or any other gases and/or water impermeable or low permeability material. In some embodiments, the housing 1210 includes insulation to reduce or minimize heat transfer with the external environment or atmosphere. As shown in FIGS. 9-10, the gases inlet 1212 and the gases outlet 1214 can be disposed or formed in the housing 1210 on a rear side of the inline humidifier 1202. In other embodiments, the gases inlet 1212 can be disposed on a front side of the inline humidifier 1202 as shown in FIG. 7 (e.g., disposed or formed in the base 1222 of FIG. 10 or a front side of the housing 1210 of FIG. 7) or on a side or edge of the inline humidifier 1202 (e.g., a side or edge of the housing 1210) and/or the gases outlet 1214 can be disposed on a front side of the inline humidifier 1202 or on a side or edge of the inline humidifier 1202 (e.g., on a side or edge of the housing 1210).

As shown in FIGS. 7 and 9-10, the gases inlet 1212 can be positioned proximate an outer perimeter of the inline humidifier 1202 or closer to the outer perimeter than a center of the inline humidifier 1202. The gases outlet 1214 can be positioned at or proximate a center of the inline humidifier 1202. In other embodiments, the gases inlet 1212 can be positioned proximate the center of the inline humidifier 1202 and the gases outlet 1214 can be positioned proximate the outer perimeter of the inline humidifier 1202, both the gases inlet 1212 and the gases outlet 1214 can be positioned proximate the center of the inline humidifier 1202, both the gases inlet 1212 and the gases outlet 1214 can be positioned proximate the outer perimeter of the inline humidifier 1202, or the gases inlet 1212 and the gases outlet 1214 can be positioned at any position between the center and outer perimeter on either side of the inline humidifier 1202.

The permeable wall 1220 separates the liquid reservoir 1224 from the gases flow path 1216. The permeable wall 1220 is permeable to vapor but is substantially impermeable to gases and liquid. The permeable wall 1220 can be made of a polymer, fiber, paper, or other material. The permeable wall 1220 can be made of a porous or non-porous material. If the permeable wall 1220 is made of a porous material, the cells of the porous material can be open or closed in different percentages. The percentage of open and closed cells of the porous material can be controlled by the void size and void fraction. In some embodiments of the permeable wall 1220, an outer layer of closed cells can be created in an otherwise open cell material by quickly cooling the outer surface of the material after extrusion. The permeable wall 1220 can be made of a non-porous material such as Arnitel or Estane. The permeable wall 1220 can be made of a porous material such as foamed Arnitel or foamed Estane. The permeable wall 1220 can be made in the form of a film, mesh, web, or a foamed variant of a film, mesh, or web.

In some embodiments, the permeable wall 1220 can include or be made of a hydrophilic, hygroscopic, or microporous material. A hydrophilic material absorbs water in a vapor and/or liquid state. A hydrophilic material can be foamed and/or can include surface features to increase the effective area of the material. A microporous material, e.g., Gore-Tex, is formed in such a way that a pore size of the material is small enough to prevent or inhibit liquid (e.g., water) from passing through but large enough to allow vapor (e.g., water vapor) to pass through.

The permeable wall 1220 can be thin and designed to have a high surface area in contact with the liquid in the reservoir 1224 and the gases in the gases flow path 1216 to improve or optimize exchange of vapor into the gases. The permeable wall 1220 can have surface features to increase the effective surface area of the hydrophilic, hygroscopic, or microporous material. Such surface features can be positioned on either or both sides (i.e., the side in contact with the gases flow path 1216 and/or the side in contact with the liquid reservoir 1224) of the permeable wall 1220. For example, the permeable wall 1220 can have a textured finish, such as, for example, a finish resembling sandpaper. As another example, the permeable wall 1220 can have a pattern of protrusions, microstructures, and/or microchannels. The surface features can be applied to the permeable wall 1220 after extrusion or other processing of the material or can be formed integrally with the permeable wall 1220 during extrusion or other processing.

When prepared for use, the reservoir 1224 contains a liquid such as water. The reservoir 1224 is in thermal communication with the base 1222 or the heater 1240. In use, power is provided to the base 1222 or the heater 1240, and heat from the base 1222 or the heater 1240 heats the liquid in the reservoir 1224 to create vapor. The vapor then passes through the permeable wall 1220 to the gases flow path 1216, where the vapor humidifies gases flowing through the gases flow path 1216. The base 1222 or the heater 1240 can be a resistance heater and can allow for improved or optimum transfer of energy into the reservoir 1224.

Figure 11:
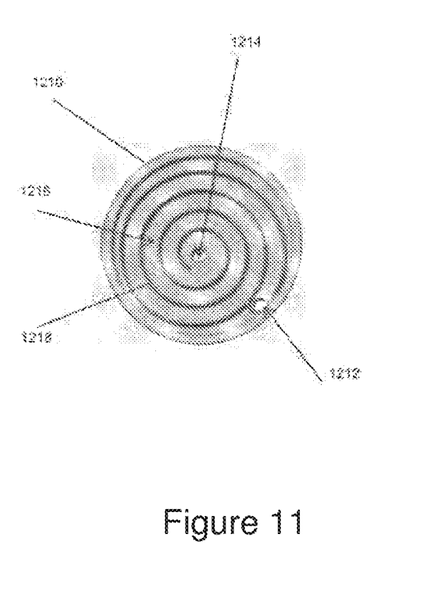
FIG. 11 illustrates a front view of the housing of the humidifier of FIGS. 9-10.

A wall 1218 within the inline humidifier 1202 defines the gases flow path 1216 extending between the inlet 1212 and the outlet 1214. The wall 1218 can be coupled to or integrally formed with an inside surface of the housing 1210 as shown in FIGS. 10-11. In other embodiments, the wall 1218 can extend from, be coupled to, or be integrally formed with the permeable wall 1220. In some embodiments, the wall 1218 can be formed by a separate insert disposed between the permeable wall 1220 and the housing 1210. In the illustrated embodiment, the wall 1218 is formed in a spiral to define a spiral arrangement of the gases flow path 1216. Other arrangements for the wall 1218 and the gases flow path 1216 are also possible. An arrangement that creates a convoluted or tortuous arrangement of the gases flow path 1216 can increase the amount of time gases in the gases flow path 1216 are in contact with the permeable wall 1220 and therefore can increase the degree or level of water vapor exchange as described in greater detail herein. In the illustrated embodiment, the wall 1218 extends perpendicularly from the rear side or surface of the housing 1210 and has a rectangular cross-sectional shape. In other embodiments, the wall 1218 can extend (from the housing 1210, from the permeable wall 1220, or as an insert separate from the permeable wall 1220 and/or the housing 1210) at an angle other than 90° relative to the rear side or surface of the housing 1210. The wall 1218 can have a cross-sectional shape other than rectangular.

In some embodiments, for example, in the illustrated embodiment in which the wall 1218 and the gases flow path 1216 are arranged in a spiral, the inlet 1212 is positioned proximate the outer perimeter of the housing 1210, and the outlet 1214 is positioned proximate the center of the housing 1210, the gases flow path 1216 follows a spiral path from an outer perimeter of the housing 1210 to a center of the housing 1210. In such an arrangement, gases in the gases flow path 1216 become warmer as the gases travel inward toward the center of the housing 1210 and to the outlet 1214, and the gases are insulated by gases in portions of the gases flow path 1216 disposed concentrically outward. If the gases flow path 1216 instead followed a path from the center of the housing 1210 to the perimeter of the housing 1210, the warmest gases at the end of the gases flow path 1216 and at the outlet 1214 would be at the outer perimeter of the housing 1210 and therefore less insulated, which could reduce the efficiency of the system. A spiral arrangement of the gases flow path 1216 can advantageously reduce or minimize flow dead spots in which the flow of gases recirculates or slows and/or can help minimize pressure losses. A gases flow path having corners and features around which the gases must flow can cause resistance to flow and increase the pressure drop through the humidifier 1202.

The humidification system 1200 or the humidifier 1202 can be supplied sterilized and ready for use. The humidification system 1200, specifically the reservoir 1224, can be prefilled (e.g., during manufacturing and assembly or set-up) with a volume of liquid, such as water, prior to a surgical procedure or other use. In some embodiments, the reservoir 1224 can be sized to hold a volume of liquid sufficient for an average duration of a typical procedure (e.g., a laparoscopic procedure or open procedure) for which the humidification system 1200 is intended to be used. The humidification system 1200 therefore does not require a separate liquid reservoir or delivery system outside of the humidifier 1202, and medical personnel need not input liquid into the system prior to use during set-up. In some embodiments, the humidifier 1202 can be refilled after use for re-use or during use if needed.

In use, gases enter the humidifier 1202 through the gases inlet 1212, flow through the gases flow path 1216, exit the humidifier 1202 through the gases outlet 1214, flow through the delivery tube 1230, and are delivered to a patient, patient interface connector, or other humidification system component at the second end 1234. Power is supplied to the base 1222 or the heater 1240 such that the base 1222 or the heater 1240 heats the liquid stored in the reservoir 1224 to form vapor that can then pass through the permeable wall 1220 into the gases flow path 1216. Gases flowing through the gases flow path 1216 are therefore humidified by the vapor passing through the permeable wall 1220. The heated vapor can also heat the gases flowing through the gases flow path 1216. The hydrophobic, impermeable, or low permeability material of the housing 1210 can help hold the vapor within the housing 1210 and prevent or inhibit the vapor from being released through the housing 1210 to the atmosphere.

The liquid reservoir 1224 can be filled and/or refilled in various ways, for example, by injecting, pumping, or pouring liquid into the reservoir 1224. In some embodiments, a vacuum can be generated within the reservoir 1224 by liquid in the reservoir 1224 becoming vapor and passing through the permeable wall 1220 into the gases flow path 1216. The vacuum can provide a pressure differential to allow for refilling of the reservoir 1224. The reservoir 1224 can also or alternatively be refilled using a water or other liquid bag. In some embodiments, the reservoir 1224 is detachable from the humidifier 1202 such that the reservoir 1224 can be refilled and/or replaced.

In some embodiments, the humidifier 1202 or the humidification system 1200 can include a supplemental liquid storage section. A longer medical procedure, or a procedure with higher gas flow requirements such as open surgery, may require greater amounts of liquid to ensure the required or desired relative humidity is maintained for the duration of the procedure. A supplemental liquid storage section can provide additional liquid storage and supply in addition to the liquid stored in the liquid reservoir 1224. In some embodiments, only the reservoir 1224 is in contact with the permeable wall 1220. The reservoir 1224 and the supplemental liquid storage section can be connected such that liquid can pass between the reservoir 1224 and the supplemental liquid storage section. For example, in some embodiments, a supplemental liquid storage section is connected to the reservoir 1224 via a connector, such as a tube, that allows liquid to flow between the reservoir 1224 and the supplemental storage section. The connector can be sized such that a flow rate between the supplemental storage section and the reservoir 1224 is greater than, but close to, a rate of vapor transfer through the permeable wall 1220. Liquid can be transferred from the supplemental storage section to the reservoir 1224 via gravity, active means such as a pump, and/or passive means such as a wicking material.

In some embodiments, the reservoir 1224 and/or the supplemental storage section can be detachable from the humidifier 1202 and may therefore be replaceable. In some embodiments, the reservoir 1224 and/or the supplemental storage section are integrally formed or permanently coupled to or disposed within the humidifier 1202. The reservoir 1224 and/or the supplemental storage section can be sealed and not refillable. In other embodiments, the reservoir 1224 and/or the supplemental storage section can be refillable with the use of specialized tools and/or a specialized process. Requiring specialized tools and/or a specialized process can restrict the ability of unqualified individuals to tamper with the reservoir 1224 and/or the supplemental storage section. In some embodiments, the reservoir 1224 and/or the supplemental storage section has an opening through which the reservoir 1224 and/or the supplemental storage section can be filled or refilled. The opening can be covered and sealed (either temporarily such that the reservoir and/or supplemental storage section can be refilled or permanently after initial manufacturing and assembly) with a lid, cap, or other sealing apparatus to seal the reservoir 1224 and/or the supplemental storage section from the external environment. The seal can be gas and/or liquid tight. If the reservoir 1224 and/or the supplemental storage section are sealed in a gas tight manner, the reservoir 1224 and/or the supplemental storage section can include a bleed valve (not shown). The bleed valve allows air into the reservoir 1224 and/or the supplemental storage section to help equalize pressure within the reservoir 1224 and/or the supplemental storage section with the pressure of the external environment. In some embodiments, at least a portion of the permeable wall 1220 can be gases permeable and can act as a bleed valve to allow gases from the gases flow path 1216 to pass through the portion of the permeable wall 1220 into the reservoir 1224 and/or the supplemental storage section to help equalize the pressure.

In use, the humidified and/or heated gases flowing through the gases flow path 1216 exit the housing 1210 through the gases outlet 1214 and flow into and through the delivery tube 1230. As shown in FIG. 7, the delivery tube 1230 can also include one or more heating elements 1250. The heating elements 1250 can heat and/or help maintain a temperature of the humidified gases flowing through the delivery tube 1230 to a patient. The humidification system 1200 therefore can employ a two-stage heating process. The humidifier 1202 can generate humidity at a reasonably or generally consistent absolute humidity level based on the amount of energy or power supplied to the base 1222 or the heater plate 1240. Subsequently, the heating elements 1250 in the delivery tube 1230 can help maintain the temperature of the gases to deliver humidity to a patient at a reasonably or generally consistent relative humidity level.

In some embodiments, vapor can pass through a hydrophilic embodiment of the permeable wall 1220 passively and/or without requiring heat. The heater plate 1240 therefore may not be required or included in the humidifier 1202, or the base 1222 may not need to act as a heater. In some such embodiments, a concentration gradient drives movement of the water or vapor across the permeable wall 1220 to the gases flow path 1216.

The humidification system 1200 can include a control system. The humidification system 1200 can include a power source for supplying power to the base 1222, the heater plate 1240, the heating elements 1250, and/or the control system. The control system can control the power supplied to the base 1222 or the heater plate 1240 to control the amount of heat provided by the base 1222 or the heater plate 1240, which in turn controls or affects the amount of vapor that is formed and passes through the permeable wall 1220 to the gases flow path 1216. The humidifier 1202 can therefore provide for passive water vapor delivery and does not require active control of the vapor delivery. The control system can also or alternatively control the power supplied to the heating elements 1250 to control or affect a temperature of gases flowing in the delivery tube 1230 and delivered to a patient.

The control system and/or power source can be external to the humidifier 1202 and/or the delivery tube 1230. The control system and/or power source can be housed within or integrated into a single housing or component. In some embodiments, the control system and/or power source can be mounted to a surgical tower or an insufflator. In some embodiments, the control system and/or power source can be connected to and receive power from a wall outlet.

Figure 12:
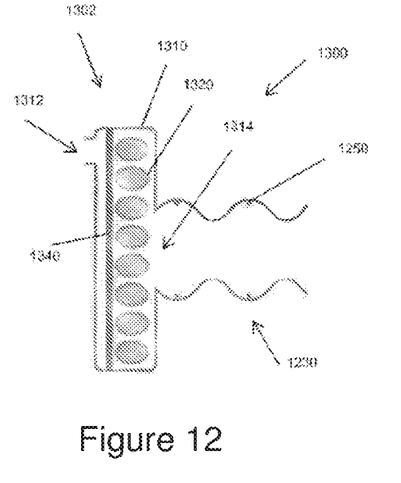
FIG. 12 illustrates a longitudinal cross-sectional view of a schematic of another example embodiment of a humidification system including an inline humidifier.
Figure 13:
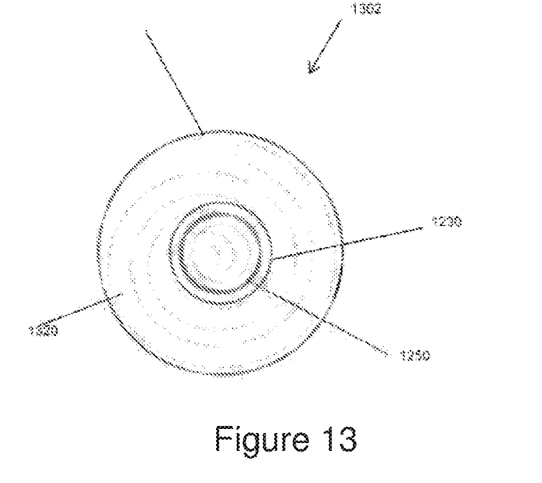
FIG. 13 illustrates a rear cross sectional view of the humidification system of FIG. 12.

FIGS. 12 and 13 illustrate another example embodiment of a humidification system 1300 including an inline humidifier 1302 according to the present disclosure. The humidifier 1302 includes a housing 1310 having an inlet 1312 and an outlet 1314, a heater 1340, and a permeable tube 1320. In the illustrated embodiment, the permeable tube 1320 is disposed in a spiral, although other configurations are also possible. The permeable tube 1320 can define or surround a liquid reservoir therein, and a gases flow path can be defined around the permeable tube 1320 between the inlet 1312 and the outlet 1314. The permeable tube 1320 can be in thermal communication with the heater 1340. In use, power can be supplied to the heater 1340 to heat the liquid within the tube 1320 to form vapor, and the vapor can pass through the permeable wall of the tube 1320 into the gases flow path. In some embodiments, the permeable tube 1320 can define or surround the gases flow path, and the permeable tube 1320 can be disposed in a liquid reservoir within the housing 1310 in thermal communication with the heater 1340. In use, power can be supplied to the heater 1340 to heat the liquid in the reservoir to form vapor, and the vapor can pass through the permeable wall of the tube 1320 into the gases flow path within the tube 1320.

The humidification system 1300 can include a control system and/or power source and/or can share other features described herein with respect to the humidification system 1100 and the humidification system 1200.

Reference throughout this specification to "permeable" materials, including but not limited to permeable walls and membranes, should be understood to include materials that generally allow the passage or diffusion of vapour, but generally inhibit the passage or diffusion of liquid and gases, through the material. Such materials can also be referred to as breathable materials.

Although reference has been made throughout this specification regarding surgical procedures, such as laparoscopic surgery, the disclosed apparatus and systems can be applied to different medical fields, for example, respiratory assistance or therapy systems.

It should be noted that various changes and modifications to the presently preferred embodiments described herein will be apparent to those skilled in the art. Such changes and modifications may be made without departing from the spirit and scope of the apparatus and systems of the disclosure and without diminishing its attendant advantages. For instance, various components may be repositioned as desired. It is therefore intended that such changes and modifications be included within the scope of the apparatus and systems of the disclosure. Moreover, not all of the features, aspects and advantages are necessarily required to practice the present apparatus and systems of the disclosure. Accordingly, the scope of the present apparatus and systems of the disclosure is intended to be defined only by the claims that follow.

Reference to any prior art in this specification is not, and should not be taken as, an acknowledgement or any form of suggestion that that prior art forms part of the common general knowledge in the field of endeavour in any country in the world.

Wherein the foregoing description reference has been made to integers or components having known equivalents thereof, those integers are herein incorporated as if individually set forth.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to"

The apparatus and system of the disclosure may also be said broadly to consist in the parts, elements and features referred to or indicated in the specification of the application, individually or collectively, in any or all combinations of two or more of said parts, elements or features.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A humidifier comprising:
   an inlet and an outlet and a gases flow path extending from the inlet to the outlet;
   a liquid reservoir in thermal communication with, or configured to be in thermal communication with in use, a heater; and
   a permeable wall separating the liquid reservoir from the gases flow path;
   wherein, in use, the heater heats liquid stored in the liquid reservoir to form vapour, and the vapour passes through the permeable wall to humidify gases in the gases flow path,
   wherein the gases flow path is defined by a spirally wound wall.

2. The humidifier of claim 1, wherein the reservoir is configured to hold sufficient liquid to produce vapour for an intended volume of gases passing through the humidifier.

3. The humidifier of claim 1, wherein the humidifier comprises a hydrophobic housing.

4. The humidifier of claim 1, wherein the permeable wall comprises a tape.

5. A humidification system comprising the humidifier of any one of the preceding claims.

6. The humidification system of claim 5, comprising a delivery tube coupled to the outlet and configured to, at least in part, transport gases from the humidifier to a patient in use.

7. The humidification system of claim 6, wherein the delivery tube comprises a second heater or heating mechanism.

8. The humidification system of claim 7, wherein the second heater or heating mechanism comprises at least one heater wire disposed within the delivery tube.

9. The humidifier of claim 1, further comprising a housing that encloses the gases flow path.

10. The humidifier of claim 9, wherein the permeable wall is positioned between the housing and the heater.

11. The humidifier of claim 9, wherein the reservoir is configured to be detachable from the housing.

12. The humidifier of claim 9, further comprising a base coupled to the housing.

13. The humidifier of claim 12, wherein the permeable wall is positioned between the housing and the base.

14. The humidifier of claim 12, wherein the base comprises a hydrophobic material and/or a liquid impermeable material.

15. The humidifier of claim 12, wherein the base comprises a thermally conductive material and/or a thermally insulating material.

16. The humidifier of claim 9, wherein the inlet and the outlet are integral with the housing.

17. The humidifier of claim 9, wherein the outlet is positioned at or near a center of the housing.

18. The humidifier of claim 9, wherein the inlet is positioned at or near an outer periphery of the housing.

19. The humidifier of claim 1, wherein the outlet is positioned at or near a center of the humidifier.

20. The humidifier of claim 1, wherein the inlet is positioned at or near an outer periphery of the humidifier.

21. The humidifier of claim 1, wherein the permeable wall comprises a hydrophilic material, a hygroscopic material, or a microporous material.

22. The humidifier of claim 1, wherein the heater comprises a heater plate.

\* \* \* \* \*